United States Patent [19]

Newport, III et al.

[11] 4,119,632

[45] Oct. 10, 1978

[54] METHOD OF PROMOTING THE CRYSTALLIZATION OF PICLORAM

[75] Inventors: John J. Newport, III; Bobby G. Messick, both of Lake Jackson, Tex.

[73] Assignee: The Dow Chemical Company, Midland, Mich.

[21] Appl. No.: 773,574

[22] Filed: Mar. 2, 1977

[51] Int. Cl.² .................. C07D 213/79; B01J 17/02; B01D 21/01; B01D 9/02
[52] U.S. Cl. .................. 260/295 R; 260/295.5 R; 23/300; 210/51; 210/54
[58] Field of Search .................. 260/295 R, 295.5 R; 23/300, 175; 210/51, 54

[56] References Cited

PUBLICATIONS

"Chem. of Acrylamide," Cyanamid Company, Process Chem. Division, 1969, pp. 37 and 41.
Libor, Chem. Abst. vol. 72, 1970, p. 165, paragraph 14822t.

Primary Examiner—Natalie Trousof
Assistant Examiner—Cary Owens
Attorney, Agent, or Firm—Daniel L. De Joseph; C. Kenneth Bjork; William M. Yates

[57] ABSTRACT

A process for promoting the spherical crystallization of picloram, wherein an anionic polymeric acrylamide flocculating agent, when combined with a solution of picloram in an aqueous sulfuric acid medium, serves to promote the formation of polycrystalline picloram spheres and to greatly reduce the formation of fines.

7 Claims, No Drawings

METHOD OF PROMOTING THE CRYSTALLIZATION OF PICLORAM

BACKGROUND OF THE INVENTION

Acrylamide polymers have long been used as flocculating agents for minerals, coal, sewage and industrial wastes. These flocculating agents serve to bring together small, electrically charged, particles to form larger agglomerates, often highly porous in nature. The floc is loosely formed and upon drying, the small-sized particles are still evident. The floc is readily broken up by agitation into small particles. The use of anionic acrylamide polymer flocculants to promote the spherical crystallization of an organic molecule is not taught in the prior art.

SUMMARY OF THE INVENTION

This invention is concerned with an improved method of promoting the spherical crystallization of picloram, which is the common name for 4-amino-3,5,6-trichloropicolinic acid.

In conventional preparative and purification procedures where picloram is crystallized by altering the acidity and/or temperature of an aqueous solution, picloram tends to crystallize primarily as small needle-like fines, i.e., particles less than 105 microns in diameter, which tend to form a mush in the mother liquor. Centrifuging and washing of this mush is time consuming and may result in a significant loss of the final product through the centrifuge screen.

One advantage, therefore, of the method of the present invention is that it reduces the amount of fines and promotes the crystallization of picloram as dense polycrystalline spheres which are greater than 105 microns in diameter. These spheres can be readily washed free of the mother liquor without an undue loss of the final product.

In accordance with the present invention, an aqueous solution containing an anionic polymeric acrylamide flocculating agent is used to dilute an aqueous sulfuric acid solution of picloram to effect the crystallization of the picloram. The presence of the flocculating agent serves to promote the formation of polycrystalline spheres and to reduce the formation of fines.

DESCRIPTION OF THE INVENTION

In the process of the present invention, anionic polymeric acrylamide flocculating agents are utilized to promote the spherical crystallization of picloram, from an aqueous sulfuric acid solution. This process also serves to reduce the formation of fines.

The flocculating agent is generally added to the dilution water which is metered together with a solution of picloram in aqueous sulfuric acid into a stirred vessel. However, it is understood that, depending on the needs of the individual practitioner of this invention, the flocculating agent can be present in the vessel before the addition of the picloram is begun, or the flocculating agent can be added to the vessel in increments during the crystallization period. As the addition of the dilution water and of the solution of picloram in sulfuric acid proceeds, crystallization and orientation of the picloram crystals from a limited number of sites occur to form large masses of crystals bonded together in spherical shapes. Upon drying, these larger crystal masses remain intact. Apparently, the crystals bond together in a mass radiating from a center which results in the formation of dense polycrystalline balls.

It is understood that the sulfuric acid solution of picloram, flocculating agent, and dilution water can be combined in any manner that is convenient to the individual practitioner of this invention. For example, a batch or semi-batch process may be used where the flocculating agent is added to the heel from a previous batch before the addition of the picloram solution and dilution water is begun. Alternately, a continuous process may be used where the dilution water containing the flocculating agent is metered simultaneously with the picloram solution into the stirred vessel and a slurry of the crystallized picloram removed at a rate to maintain a level in the vessel. Other variations which are obvious to those skilled in the art are intended to be within the scope of the present invention.

Flocculating agents which may be employed in the improved method of the present invention are water soluble, anionic acrylamide polymers such as, for example, Purifloc® A22, Purifloc® A23, and Purifloc® A25 flocculants, which are well known to the art-skilled persons.

During polymerization, there is some degree of hydrolysis of the acrylamide's —$CONH_2$ group to —COOH. As used herein, the term "anionic" refers to those acrylamide polymers which contain greater than one percent of carboxyl or which will hydrolyze in aqueous sulfuric acid to form greater than one percent of carboxyl.

The optimum amount of anionic polyacrylamide flocculating agent to be employed in combination with the picloram-aqueous sulfuric acid medium solution will be dependent upon such variable factors as the temperature of the solution, the acidity of the aqueous acid medium, the purity of the picloram, and the particular flocculating agent utilized. Generally, an effective crystallization-promoting amount is at least about 10 parts by weight of the flocculating agent per million parts (ppm) by weight of the solution and usually an amount from about 20 ppm to about 40 ppm is suitable. It is understood that the weight of the solution is equivalent to the combined weight of the picloram, the dilution water, and the aqueous sulfuric acid medium. Ordinarily such solutions will contain from about 2 to about 19 weight percent of picloram and from about 30 to 80 weight percent sulfuric acid.

The operable crystallization temperature will vary from about 20° C to about 90° C. Generally, however, any temperature at which the picloram will crystallize from an aqueous sulfuric acid medium is suitable for the purposes of this invention. It is understood that the acceptable amount of crystallization will be determined by the individual practitioner of this invention. At temperatures above about 90° C, a significant amount of picloram tends to remain in solution. Thus, the individual may choose to maintain the solution temperature at that range in which solubility losses will be minimized. Generally, the preferred temperature range is from about 40° C to about 75° C.

EXAMPLES

The following examples are given solely for the purpose of illustration and are not to be construed as limitations of this invention, many variations of which are possible without departing from the spirit or scope thereof.

A laboratory crystallizer consisting of a baffled one-liter round bottom flask was charged with 100 ml aqueous 30 weight percent sulfuric acid containing 20 ppm by weight Purifloc ® A23 flocculating agent. The solution was heated to 60° C and stirred. A solution containing 105 gm picloram in 395 gm aqueous 75% by weight sulfuric acid at 120° C was fed into the crystallizer simultaneously with an aqueous solution containing 36 ppm by weight Purifloc ® A23 at 25° C. The mixture in the crystallizer was stirred at a rate to keep the crystallized picloram suspended throughout the solution. The feed rates were adjusted to maintain the aqueous phase in the crystallizer at about 30% to 35% by weight sulfuric acid. Thus, about 20 ppm by weight Purifloc ® A23 was maintained in the crystallizer throughout the crystallization. The mixture in the crystallizer was kept at 60°–70° C throughout the crystallization, about one hour. The crystallized product was filtered on a Buchner funnel and washed with about 300 ml distilled water. After drying the picloram solids in a fan-forced oven at 80° C, a particle size distribution was determined using standard mesh screens. Table I shows the percent of particles in each size range. Even many particles below 105 microns in diameter are spherical and not needle-like as in the prior art.

TABLE 1

Particle Size Distribution

| Particle size (Diameter in Microns) | Percent |
|---|---|
| >841 | 0.15 |
| 841–595 | 1.1 |
| 595–250 | 90.0 |
| 250–177 | 6.75 |
| 177–149 | 1.1 |
| 149–105 | 0.6 |
| <105 | 0.3 |

The experiment was repeated with 30 ppm of Purifloc ® A23 maintained in the crystallizer.

Table 2 shows the results of the particle size distribution determination.

TABLE 2

| Particle Size (Diameter in Microns) | Percent |
|---|---|
| >841 | * |
| 841–595 | 0.3 |
| 595–250 | 21.1 |
| 250–177 | 48.7 |
| 177–149 | 18.8 |
| 149–105 | 10.4 |
| <105 | 0.6 |

*less than 0.1 percent

The experiment was repeated with 10 ppm of Purifloc ® A23 maintained in the crystallizer.

Table 3 shows the results of the particle size distribution determination.

TABLE 3

| Particle Size (Diameter in Microns) | Percent |
|---|---|
| >841 | 0.15 |
| 841 – 595 | 4.39 |
| 595 – 250 | 6.79 |
| 250 – 177 | 10.24 |
| 177 – 149 | 9.97 |
| 149 – 105 | 12.95 |

TABLE 3-continued

| Particle Size (Diameter in Microns) | Percent |
|---|---|
| <105 | 55.22 |

The experiment was repeated with no Purifloc ® A23 being used in the crystallizer. A mush was formed composed of needle-like crystals of picloram <105 microns in size suspended in the aqueous sulfuric acid medium with no evidence of dense polycrystalline balls being formed. Drying of the picloram product produced a cake that could not be screened without crushing.

The experiment was repeated except that a second lot of picloram was used to prepare the 105 gm picloram-395 gm 75% aqueous sulfuric acid feed solution and with 40 ppm of Purifloc ® A23 maintained in the crystallizer.

Table 4 shows the results of the particle size distribution determination.

TABLE 4

| Particle Size (Diameter in Microns) | Percent |
|---|---|
| >841 | 0.22 |
| 841 – 595 | 2.12 |
| 595 – 250 | 48.77 |
| 250 – 177 | 32.87 |
| 177 – 149 | 6.05 |
| 149 – 105 | 4.76 |
| <105 | 5.95 |

While sulfuric acid has been employed in the examples, other acids such as HCl, $H_3PO_4$, $HNO_3$ and the like may be used to form the acid solution of the present invention.

What is claimed is:

1. A method for promoting the spherical crystallization of picloram, which comprises combining an anionic polyacrylamide flocculating agent, picloram, and an aqueous acidic medium, wherein the flocculating agent is present in an amount of at least about 10 parts by weight of the flocculating agent per million parts by weight of the combined weight of the picloram and the aqueous acid medium.

2. The method of claim 1 wherein the amount of flocculating agent ranges from about 20 to about 40 parts by weight of the flocculating agent per million parts by weight of the combined weight of the picloram and the aqueous acid medium.

3. The method of claim 1 wherein the aqueous acid medium is 30% to 35% $H_2SO_4$ by weight.

4. The method of claim 1 wherein the crystallization temperature is maintained at from about 40° C to about 75° C.

5. The method of claim 1 wherein the flocculating agent is selected from the group consisting of Purifloc ® A22, Purifloc ® A23 and Purifloc ® A25.

6. The method of claim 5 wherein the flocculating agent is Purifloc ® A23.

7. The method of claim 1 wherein the flocculating agent is Purifloc ® A23, the aqueous acid medium is 30% to 35% $H_2SO_4$, the amount of flocculating agent ranges from about 20 to about 40 parts by weight of the flocculating agent per million parts by weight of the combined weight of the picloram and the aqueous acidic medium, and the crystallization temperature is maintained at about 60° C to about 70° C.

* * * * *